United States Patent [19]

Petersen

[11] Patent Number: 4,833,030
[45] Date of Patent: May 23, 1989

[54] POLYMER IMPREGNATED AND CARBONIZED CARBON/CARBON COMPOSITE

[75] Inventor: Robert B. Petersen, Los Angeles, Calif.

[73] Assignee: Hitco, Irving, Calif.

[21] Appl. No.: 927,967

[22] Filed: Nov. 7, 1986

Related U.S. Application Data

[62] Division of Ser. No. 755,800, Jul. 17, 1985, Pat. No. 4,623,735, which is a division of Ser. No. 611,729, May 18, 1985, Pat. No. 4,588,799.

[51] Int. Cl.$^4$ ................................................. B32B 9/00
[52] U.S. Cl. ................................ 428/408; 244/158 A; 427/228; 264/29.5; 428/689; 428/698
[58] Field of Search ............... 427/228; 502/182, 185, 502/416, 417; 264/29.5; 428/408

[56] References Cited

U.S. PATENT DOCUMENTS

| | | | |
|---|---|---|---|
| 3,793,224 | 2/1974 | Cooper | 502/185 |
| 3,806,466 | 4/1974 | Bird et al. | 502/185 |
| 4,185,043 | 1/1980 | Shaffer | 525/364 |
| 4,321,298 | 3/1982 | Shaffer | 427/228 |
| 4,472,476 | 9/1984 | Veltri et al. | 428/408 |
| 4,540,764 | 9/1985 | Hinman | 528/9 |
| 4,588,799 | 5/1986 | Peterson | 528/9 |
| 4,591,578 | 5/1986 | Foley et al. | 502/185 |
| 4,623,735 | 11/1986 | Peterson | 549/206 |

OTHER PUBLICATIONS

G. W. A. Fowles et al., Inorganic Chemistry, vol. 3, No. 2, Feb. 1964, pp. 257–259.
C. S. Kraihanzel et al., Inorganic Chemistry, vol. 2(3), Jun, 1963, pp. 533–540.
J. A. Connor et al., Jour. Organometallic Chemistry, vol. 24, (1970), pp. C20–C22.

*Primary Examiner*—Paul E. Konopka
*Attorney, Agent, or Firm*—Roylance, Abrams, Berdo & Goodman

[57] ABSTRACT

Metal complexes are obtained by reacting furfurylamine with a metal carbonyl selected from the group consisting of tungsten carbonyl, molybdenum carbonyl and chromium carbonyl. Multi-cycle reimpregnation polymers are obtained by reacting one of these metal complexes with furfuryl alcohol. A carbon/carbon composite is formed by impregnating a carbon/carbon composite containing voids with said polymer and curing and carbonizing said polymer.

4 Claims, No Drawings

POLYMER IMPREGNATED AND CARBONIZED CARBON/CARBON COMPOSITE

This is a division of application Ser. No. 755,800, filed July 17, 1985, now U.S. Pat. No. 4,623,735, which is a division of application Ser. No. 611,729, filed May 18, 1985, now U.S. Pat. No. 4,588,799.

BACKGROUND OF THE INVENTION

This invention relates to thermosetting, solventless polymers containing variable ratios of tungsten, molybdenum or chromium chemically bonded in the polymer chain which have high char yield and which are particularly useful for multi-cycle reimpregnation of a carbon/carbon composite.

With the advent of aerospace products, carbon/carbon composites having high densities have come into widespread use. One or a combination of the following three methods for densification of carbon/carbon composites is commonly employed: (1) high temperature consolidation; (2) chemical vapor deposition; and (3) multi-cycle reimpregnation. For applications involving large parts or complex shapes, multi-cycles reimpregnation has been found to be the most effective method for imparting oxidation resistance and energy absorbing characteristics through the use of specifically formulated polymers.

A reimpregnation resin is a thermosetting polymer introduced as a liquid into the characteristic voids of a carbon/carbon composite. The resin is subsequently cured and heat treated, thus increasing the density of the composite. Selected polymers can be used to impart specific desired characteristics to the composite depending upon the ultimate application. Viable reimpregnation resins must maintain a suitably low viscosity during the reimpregnation process and, in addition, exhibit a relatively high char yield. "Multi-cycle reimpregnation" is the term applied when the reimpregnation process is repeated a number of times.

U.S. Pat. No. 4,185,043 to Robert C. Shaffer discloses thermoplastic and thermosetting polymers which incorporate tungsten and/or molybdenum metal atoms. The metal atoms are incorporated into the polymer by reacting a monomer or polymer containing at least one free carboxyl group with a reaction product of tungsten or molybdenum carbonyl and pyrrolidine to obtain a polymer. It is disclosed that the polymers are useful as reimpregnation resins.

SUMMARY OF THE INVENTION

It has now been discovered that the reaction product of furfurylamine and tungsten carbonyl, molybdenum carbonyl or chromium carbonyl reacts directly with furfuryl alcohol to produce a suitable multi-cycle reimpregnation polymer. The resulting dark, viscous polymer may be utilized neat or it may be diluted with furfuryl alcohol, a reactive solvent, or it may diluted with an inert solvent such as dimethylformamide. Because of the relatively low viscosity at moderate temperatures, the polymers of this inventions may be used in a multi-cycle reimpregnation process without a solvent. By appropriate choice of the amounts of reactants, precise variation in metal content may be achieved while retaining the metal in atomic form in the polymer molecule. The cured resin possesses low porosity and high char yield, characteristics which render it particularly useful for multi-cycle reimpregnation. Very little tungsten is lost during the sequence of operations resulting in the final char.

DESCRIPTION OF THE PREFERRED EMBODIMENTS

A complex is first prepared by reacting furfurylamine with a metal carbonyl selected from the group consisting of tungsten carbonyl, molybdenum carbonyl and chromium carbonyl. The reaction of sterically unhindered amines, although not furfurylamine, with metal carbonyls is well known in the art, [see G. W. A. Fowles et al, "The Reactions of Group VI Metal Carbonyls with Pyrrolidine, Piperazine and Morpholine", Vol. 3, No. 2, pages 257–259 (1964); and C. S. Kraihanzel et al, *Inorganic Chemistry*, Vol. 2, No. 3, pages 533–540 (1963)]. Preferably the complexes are prepared by reacting from 4 to 12 moles of furfurylamine per mole of metal carbonyl for from 4 to 20 hours at a temperature of from 60° to 150° C.

The furfuryl alcohol is reacted with the furfurylamine-metal complex by combining the two materials and heating the reaction mixture preferably within the range of about 25° C. to 180° C. for about 5–10 hrs. The conditions required for completion of the reaction of the furfurylamine-metal complex with furfuryl alcohol vary, depending on the ratios of reactants as set forth in the following table:

| Ratio of Moles of Complex to Furfuryl alcohol | Temp. Range | Time (Approximate) |
| --- | --- | --- |
| 1:3 | 25° C. to 160° C., then 160° C. to 170° C. | 5.0 hours 0.5 hour |
| 1:5 | 25° C. to 160° C., then 160° C. to 175° C. | 3.0 hours 1.5 hours |
| 1:7 | 25° C. to 160° C., then 160° C. to 172° C. | 5.0 hours 3.0 hours |
| 1:9 | 25° C. to 160° C., then 160° C. to 180° C. | 5.0 hours 5.0 hours |

The amount of metal in the finished resin may be controlled by varying the ratio of furfurylamine-metal complex to furfuryl alcohol in the thermoplastic polymer, and by varying the amount of furfuryl alcohol used as the reactive diluent.

The polymers of this invention have the property of being both thermoplastic and thermosetting, i.e., at temperatures of up to about 180°C. they are thermoplastic, i.e., they may be heated to obtain a low viscosity flowable material which, upon cooling, solidifies. At higher temperatures, i.e., above about 200° C., the materials are thermosetting, i.e., curable.

The following example illustrates the best mode contemplated for carrying out this invention.

EXAMPLE

A mixture of tungsten hexacarbonyl (88 g, 0.25 mole) and furfurylamine (92 ml, 1.00 mole) is heated at about 120° C. with stirring under argon for about 16 hours. To the cooled red-brown reaction mixture, 100 ml of a 50% ethanol/50% water solution is added to cause precipitation of the golden-yellow complex. The solid is isolated by vacuum filtration and washing with ethanol/water, followed by vacuum drying. The impure product is moderately air-sensitive; the pure dry product is considerably less so. However, storage excluding air is advisable. Recrystallization, if necessary, is by solution in warm, oxygen-free furfurylamine, followed by precipitation with water. The infrared spectrum of the product indicates that it is $W(CO)_4(furfurylamine)_2$. The product does not melt, but decomposes gradually above 60° C.

Furfuryl alcohol (2.08 moles) is added to 0.42 mole of the reaction product of tungsten hexacarbonyl and furfurylamine. The mixture is gradually heated to 160° C. over five hours with stirring. It is then maintained between 160°-170° C. until the desired viscosity is achieved. The resulting dark brown thermoplastic material is viscous-to-solid at room temperature, depending on the duration of heating. It can be diluted while hot with a reactive polar solvent such as furfuryl alcohol or with an inert polar solvent such as dimethyl formamide. For maximum metal loading, the resulting polymer may be used "neat" as a multi-cycle reimpregnation resin for a carbon/carbon composite by impregnating it into the voids of the composite. The polymer is then cured by heating at 200° C. for 20 hours. This cured thermoset resin, when subsequently carbonized at 800° C. for one hour, contains approximately 35% tungsten by weight. The char contains 80-90% of the tungsten present in the polymer precursor.

What is claimed is:

1. A carbon/carbon composite prepared by impregnating a carbon/carbon composite containing voids with a polymer comprising the reaction product of (1) furfuryl alcohol and (2) a metal complex comprising the reaction product of furfuryl amine and a metal carbonyl selected from the group consisting of tungsten carbonyl, molybdenum carbonyl and chromium carbonyl, curing said polymer and subsequently carbonizing said polymer.

2. A carbon/carbon composite as defined in claim 1 wherein said metal carbonyl is tungsten carbonyl.

3. A carbon/carbon composite as defined in claim 1 wherein said metal carbonyl is molybdenum carbonyl.

4. A carbon/carbon composite as defined in claim 1 wherein said metal carbonyl is chromium carbonyl.

* * * * *